(12) United States Patent
Shimokawa et al.

(10) Patent No.: US 9,791,461 B2
(45) Date of Patent: Oct. 17, 2017

(54) METHOD FOR TESTING FOR CARDIOVASCULAR DISEASE WITH CYCLOPHILIN A

(71) Applicant: TOHOKU UNIVERSITY, Miyagi (JP)

(72) Inventors: Hiroaki Shimokawa, Miyagi (JP); Kimio Satoh, Miyagi (JP)

(73) Assignee: TOHOKU UNIVERSITY, Miyagi (JP)

(*) Notice: Subject to any disclaimer, the term of this patent is extended or adjusted under 35 U.S.C. 154(b) by 0 days.

(21) Appl. No.: 14/439,170

(22) PCT Filed: Oct. 29, 2013

(86) PCT No.: PCT/JP2013/079326
§ 371 (c)(1),
(2) Date: Apr. 28, 2015

(87) PCT Pub. No.: WO2014/069490
PCT Pub. Date: May 8, 2014

(65) Prior Publication Data
US 2015/0293121 A1 Oct. 15, 2015

(30) Foreign Application Priority Data

Oct. 30, 2012 (JP) .................................. 2012-239615

(51) Int. Cl.
*G01N 33/68* (2006.01)
(52) U.S. Cl.
CPC ..... *G01N 33/6893* (2013.01); *G01N 2333/99* (2013.01); *G01N 2800/32* (2013.01)
(58) Field of Classification Search
CPC ........... G01N 33/6893; G01N 2333/99; G01N 2800/32
See application file for complete search history.

(56) References Cited

U.S. PATENT DOCUMENTS

2010/0190686 A1* 7/2010 Wells ................. G01N 33/5023 514/5.9

FOREIGN PATENT DOCUMENTS

WO 2011/041545 4/2011

OTHER PUBLICATIONS

Yan, J. et al., The clinical implications of increased cyclophilin A levels in patients with acute coronary syndromes, Clinica Chimica Acta, 2012, vol. 413, pp. 691-695.
Satoh, K. et al., Plasma cyclophilin A is a novel biomarker for coronary artery disease, Circulation Journal, 2013, vol. 77, No. 2, pp. 447-455.
Satoh, K. et al., Cyclophilin A enhances vascular oxidative stress and development of angiotensin II-induced aortic aneurysms, Nature Medicine, 2009, vol. 15, No. 6, pp. 649-656.
Satoh, K. et al., Cyclophilin A mediates vascular remodeling by promoting inflammation and vascular smooth muscle cell proliferation, Circulation, 2008, vol. 117, pp. 3088-3098.
Nigro, P. et al., Cyclophilin A is an inflammatory mediator that promotes atherosclerosis in apolipoprotein E-deficient mice, The Journal of Experimental Medicine, 2011, vol. 208, No. 1, pp. 53-66.
Satoh, K. et al., Oxidative stress and vascular smooth muscle cell growth: a mechanistic linkage by Cyclophilin A, Antioxidants & Redox Signaling, 2010, vol. 12, No. 5, pp. 675-682.
Satoh, K. et al., Cyclophilin A—promising new target in cardiovascular therapy, Circulation Journal, 2010, vol. 74, pp. 2249-2256.
International Search Report for PCT/JP2013/079326, dated Feb. 4, 2014.
Satoh et al., "Abstract 11001: Cyclophilin a Mediates Pulmonary Vascular Remodeling by Rho-Kinase Activation in Patients With Pulmonary Hypertension", Circulation, 122(21):A11001 (2010).
Satoh et al., "Abstract 11189: Plasma Cyclophilin A as a Novel Biomarker for Pulmonary Hypertension in Humans", Circulation, 126:A11189 (2012).
Extended European Search Report issued Oct. 27, 2016 in corresponding European Application No. 13850997.1.
Partial Supplementary European Search Report issued May 31, 2016 in corresponding European Application No. 13850997.1.
Soe et al.: "Cyclophilin A: A Mediator of Cardiovascular Pathology", J Korean Soc Hypertens, 17(4): 133-147(2011).

\* cited by examiner

*Primary Examiner* — Sahar Javanmard
(74) *Attorney, Agent, or Firm* — Wenderoth, Lind & Ponack, L.L.P.

(57) ABSTRACT

An object of the present invention is to provide a novel examination method for a cardiovascular disease. As means for achieving the object, provided is an examination method for a cardiovascular disease, the method including the steps of: measuring a concentration of cyclophilin A protein in a human blood sample; and determining a probability of development of a cardiovascular disease based on the measured concentration of cyclophilin A protein.

2 Claims, 10 Drawing Sheets

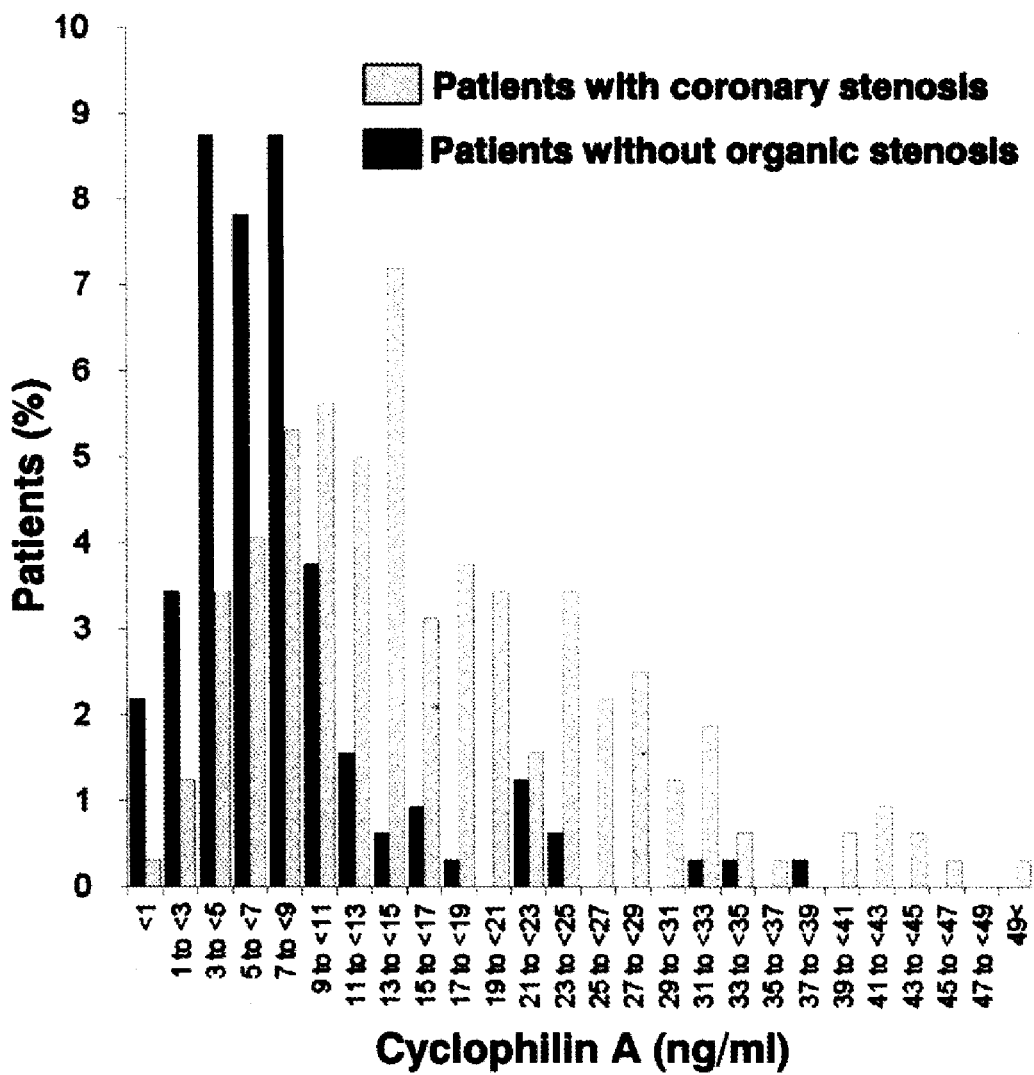
[FIG. 1]

[FIG. 2]
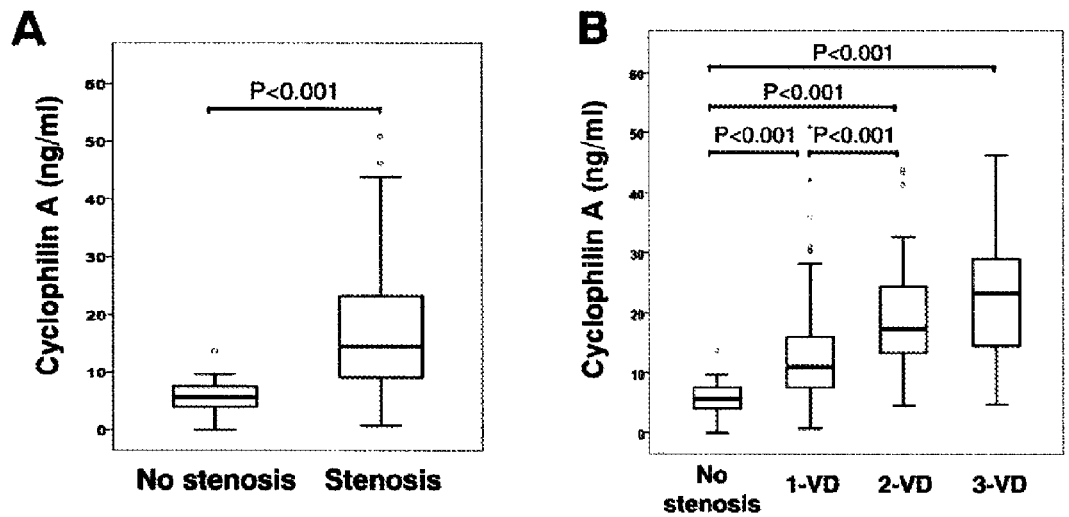
[FIG. 3]
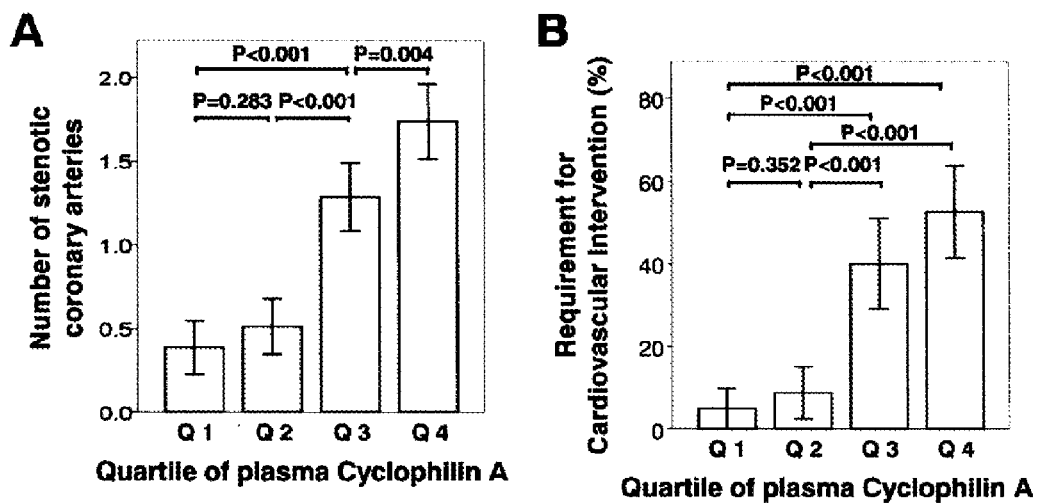

[FIG. 4]
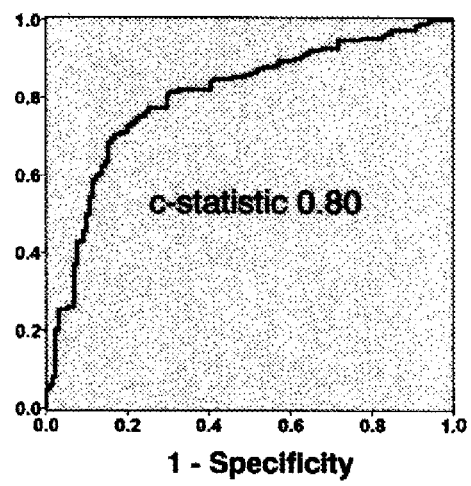
A
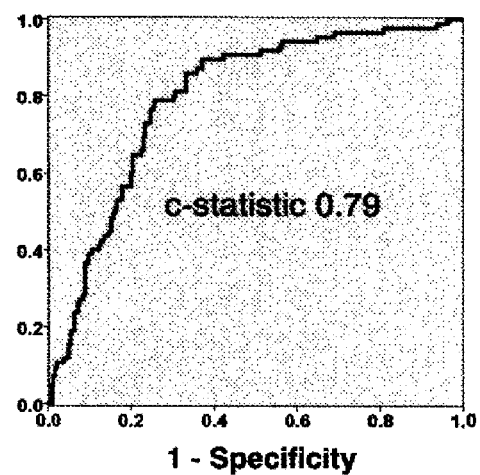
B

[FIG. 5]
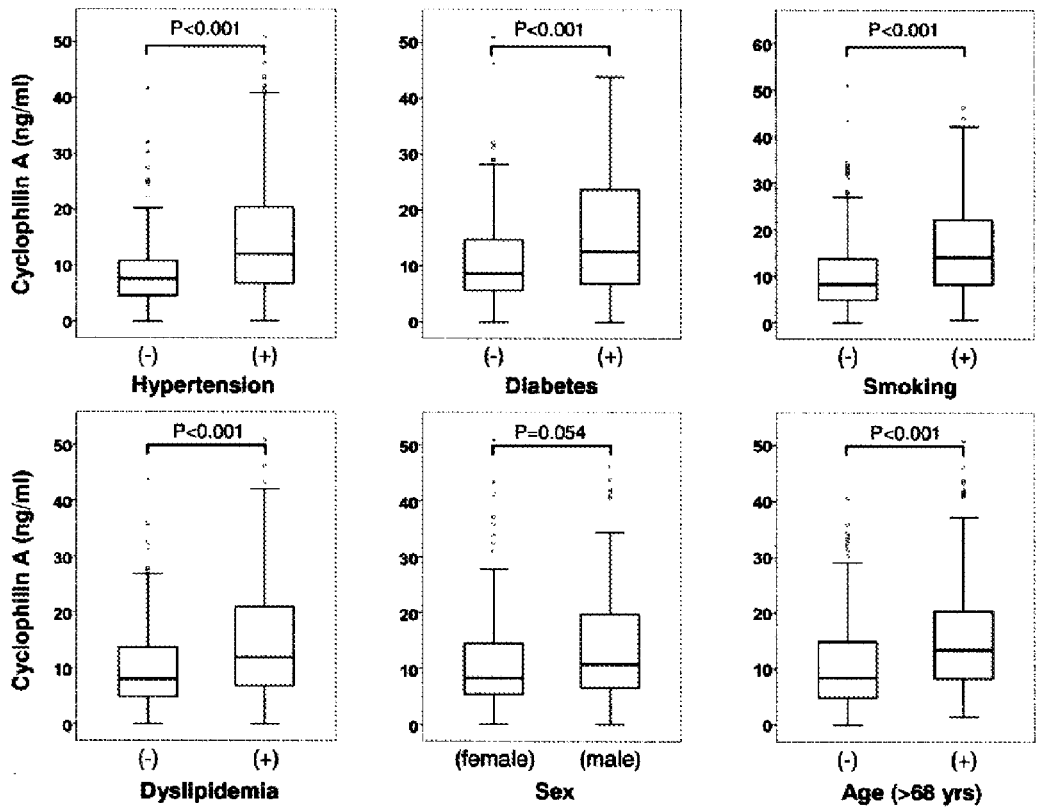
[FIG. 6]
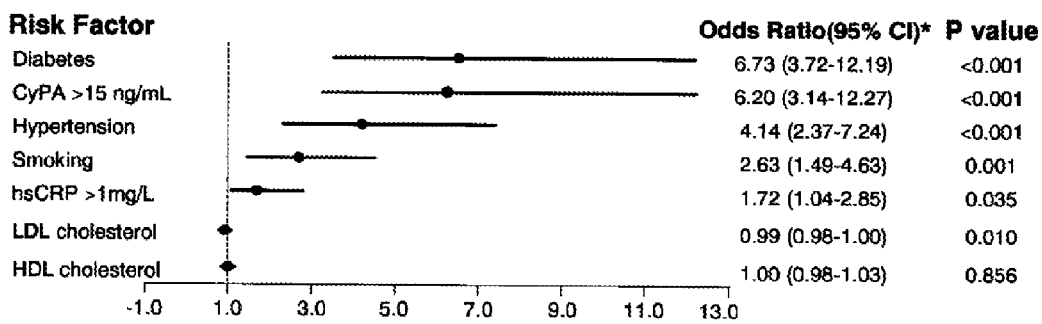

[FIG. 7]
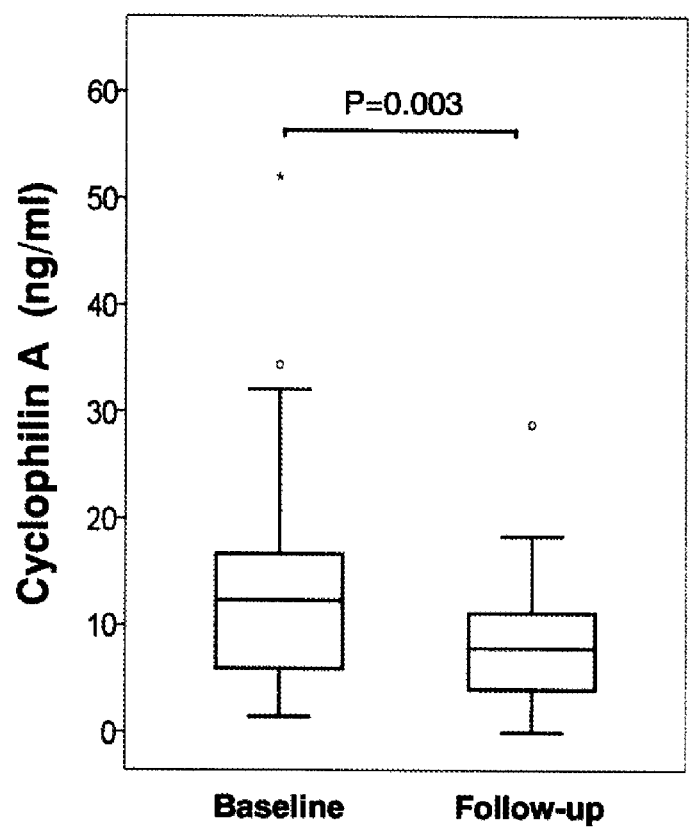

[FIG. 8]
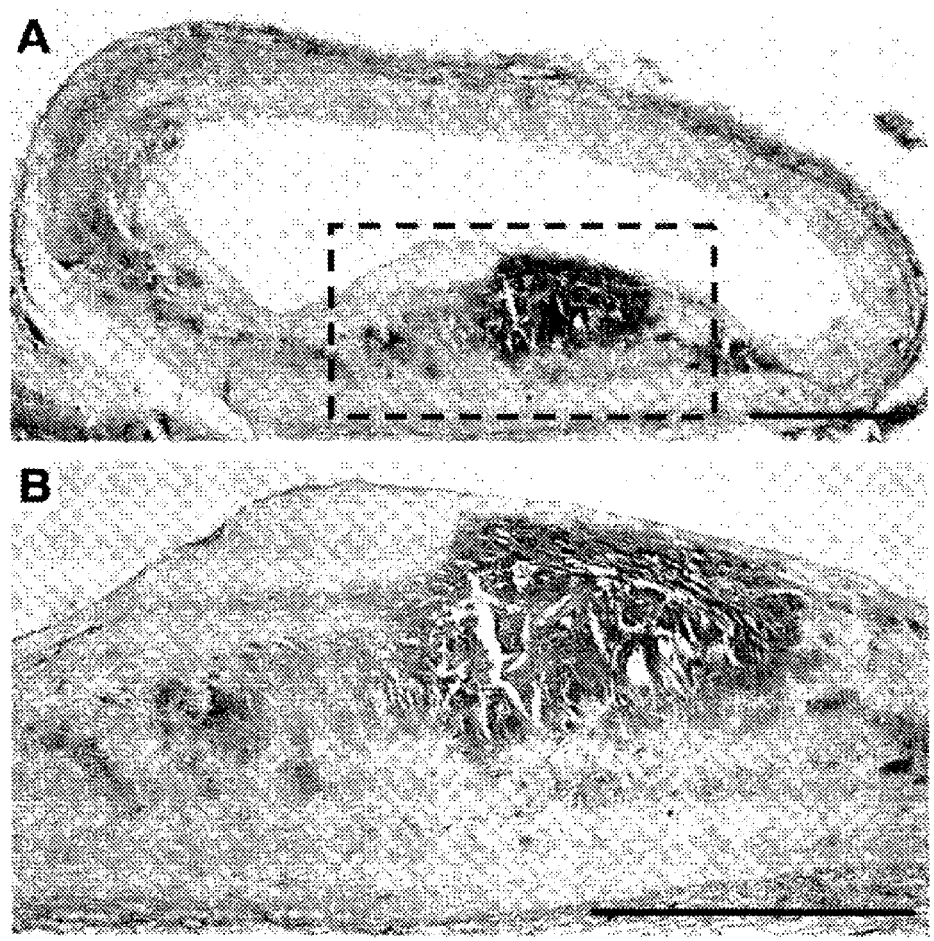

[FIG. 9]
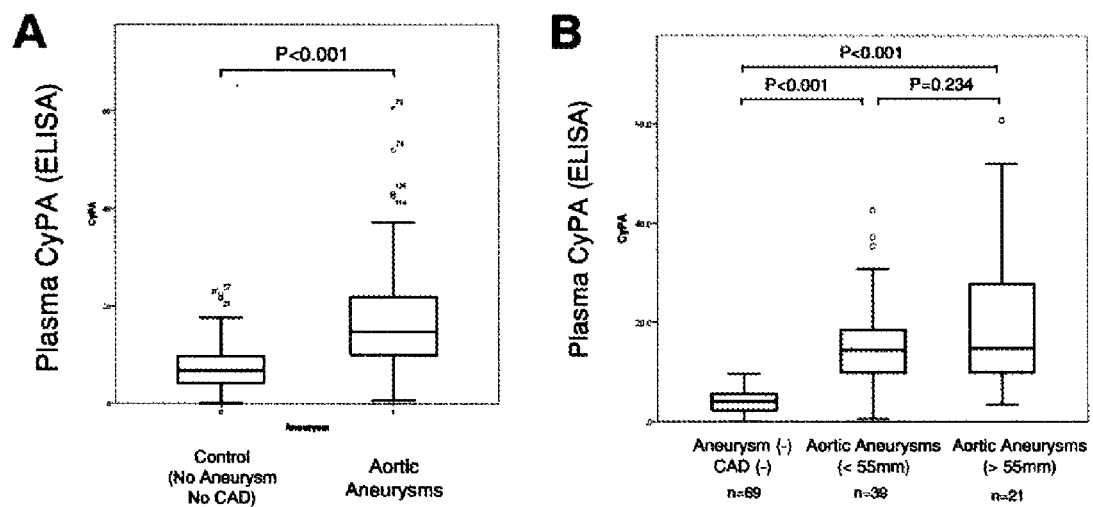
[FIG. 10]
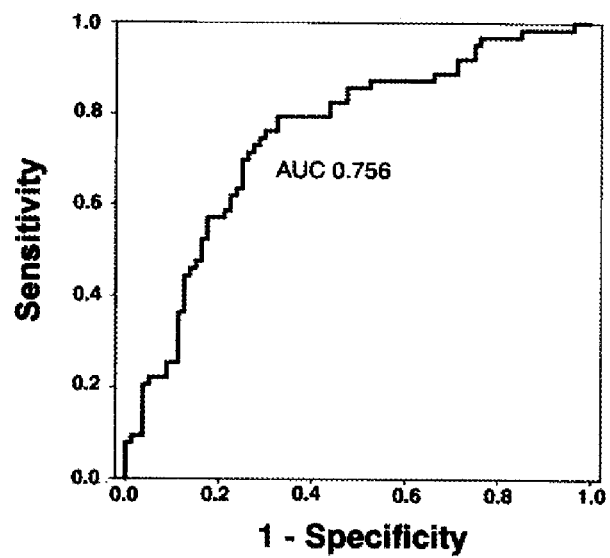

[FIG. 11]
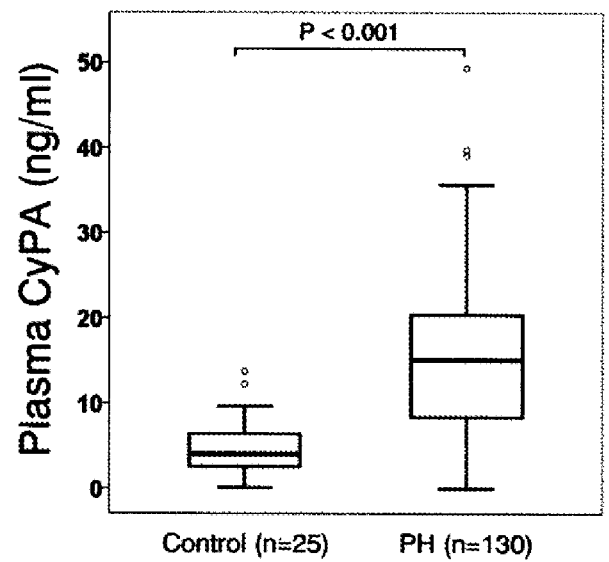
[FIG. 12]
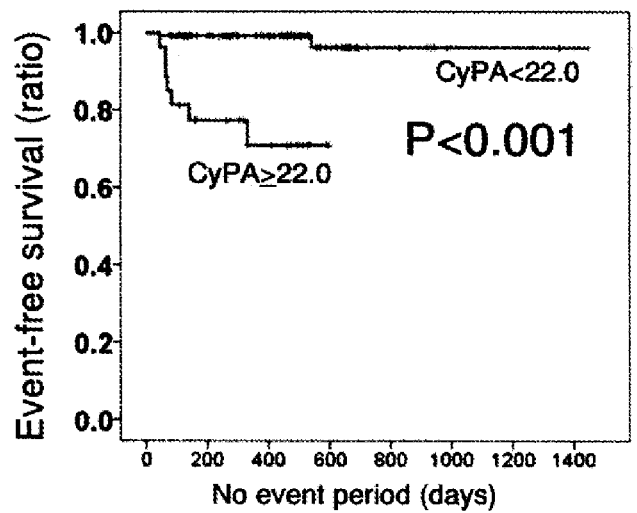

[FIG. 13]
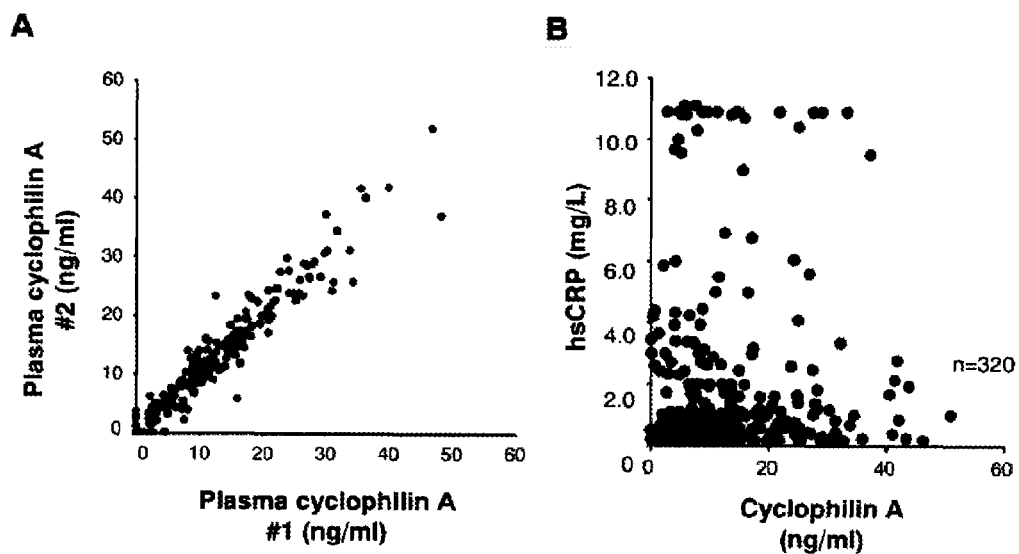
[FIG. 14]
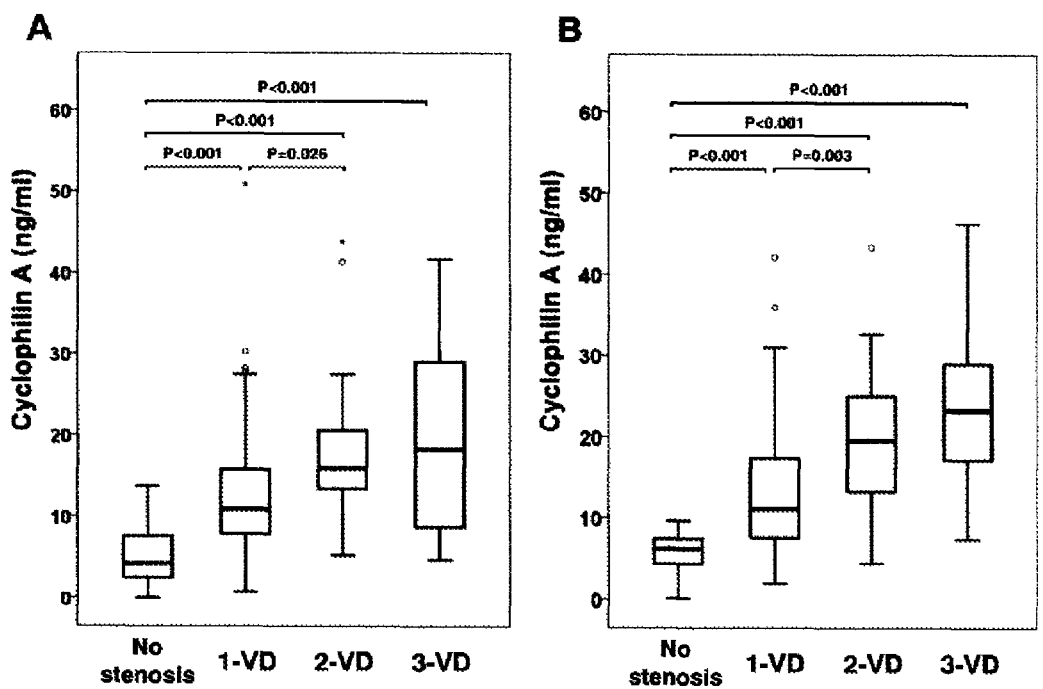

[FIG. 15]
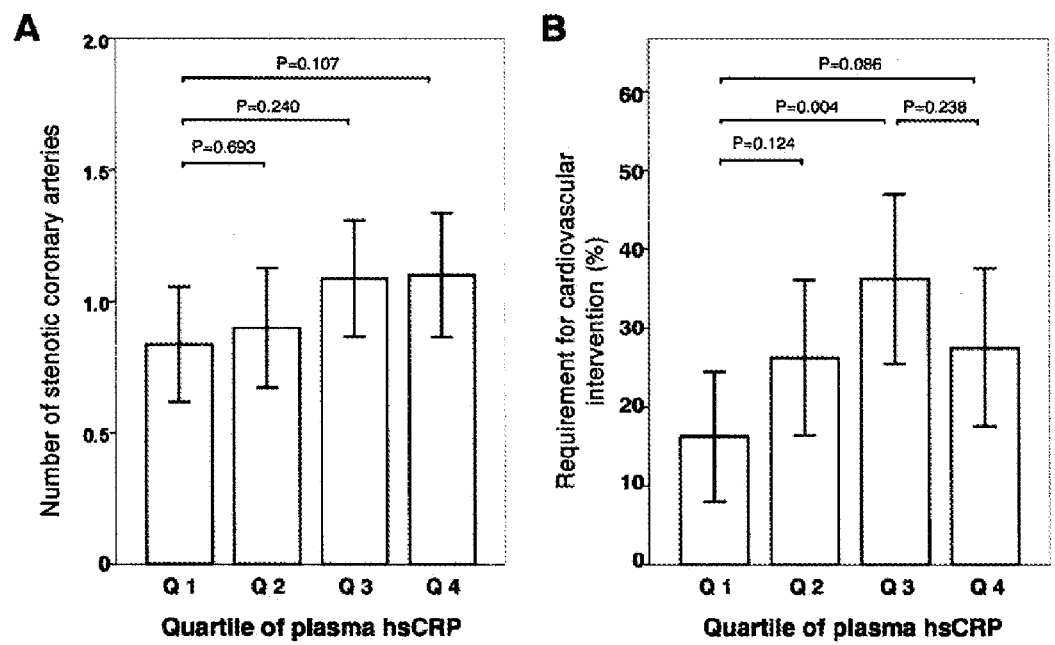
[FIG. 16]
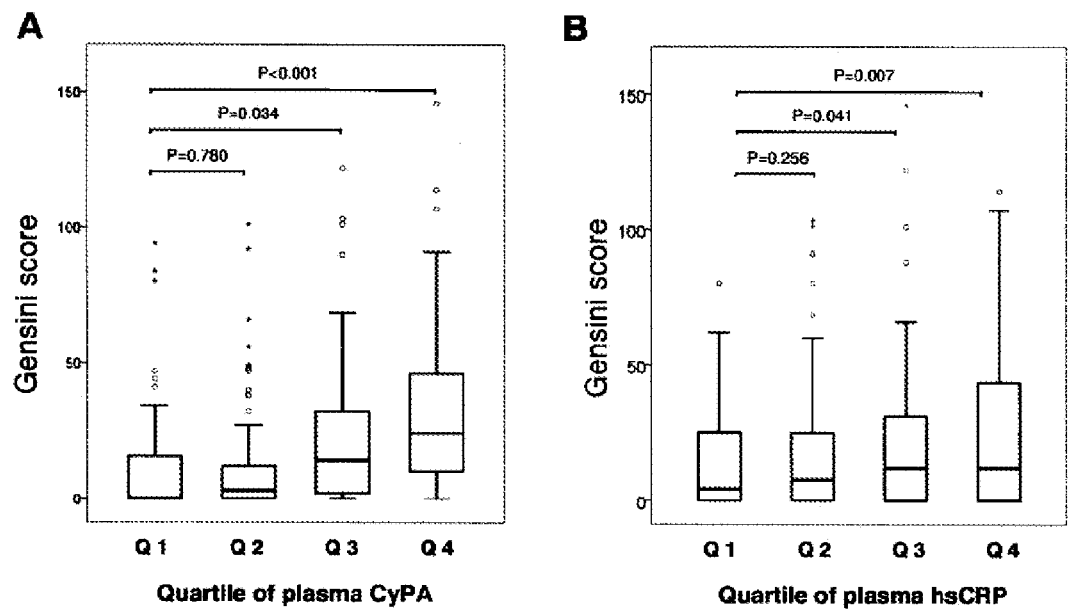

US 9,791,461 B2

METHOD FOR TESTING FOR CARDIOVASCULAR DISEASE WITH CYCLOPHILIN A

TECHNICAL FIELD

The present invention primarily relates to an examination method for a cardiovascular disease. The present invention also relates to an examination kit for a cardiovascular disease and a treatment method for a cardiovascular disease.

BACKGROUND ART

Arteriosclerosis, which is induced and progressed by various risk factors, causes thickening of the arterial lumen to interrupt blood flow, resulting in a cardiovascular disease such as aortic aneurysm, angina, myocardial infarction, or cerebral infarction. When the cardiovascular disease becomes severe, the patient may die. Therefore, the patient is desirably subjected to early diagnosis and appropriate treatments. One of the subjective symptoms of patients with the cardiovascular disease is chest pain or discomfort. However, only a small percentage of patients with chest pain or the like actually develop or have a probability of development of the cardiovascular disease. Therefore, the patients are required to be subjected to differential diagnosis by a doctor.

The presence or absence of a cardiovascular disease can be examined precisely by, for example, cardiac catheterization or angiography. However, it is necessary to insert a catheter into the vessel in the cardiac catheterization and to introduce a contrast dye into the vessel in the angiography, resulting in heavy burdens on both a subject to be examined and a healthcare professional. Further, cost burdens for the examination may increase medical costs spent by the country or the like. Therefore, it is difficult to conduct a thorough examination for all patients with subjective symptoms.

Therefore, prior to the thorough examination, the patients are subjected to differential diagnosis mainly through history taking. However, the differential diagnosis based on the history taking is insufficient in accuracy because of its large dependence on experiences of doctors.

Previous studies reported that biomarkers such as troponin T and high-sensitivity C-reactive protein (CRP) were useful in examinations for a cardiovascular disease. An increased blood troponin T level enables highly accurate diagnosis of acute myocardial infarction. However, it is difficult to examine the presence or absence of a non-severe cardiovascular disease with troponin T. In addition, high-sensitivity CRP is non-specific because the high-sensitivity CRP level increases in patients with various inflammatory diseases. Therefore, high-sensitivity CRP is not a reliable biomarker that is used in routine differential diagnosis for a cardiovascular disease even at the present day when measurement environments are sufficient.

Therefore, a method capable of examining a cardiovascular disease readily with high accuracy is now required.

Cyclophilin A (CyPA) protein encodes a chaperon protein that binds to cyclosporin. A previous study suggests that cyclophilin A protein promotes production of oxidative stress in models of abdominal aortic aneurysm, induced by angiotensin II in ApoE$^{-/-}$ mice, and is essential for generation of models of abdominal aortic aneurysm (Non Patent Literature 1). In addition, it has been reported that cyclophilin A protein is involved in angiostenosis (Non Patent Literature 2), atherosclerosis (Non Patent Literature 3), and increased production of reactive oxygen species (Non Patent Literatures 4 and 5).

However, cyclophilin A protein is known to have various functions such as infection with HIV virus (AIDS) and replication of hepatitis C virus in addition to those described above. In recent years, drug development in the infectious disease field based on such functions has attracted attention. Further, usefulness of cyclophilin A protein as a biomarker for a cardiovascular disease has been unknown heretofore. For example, there has been unknown a correlation between the presence of an actual cardiovascular disease, in particular, human cardiovascular disease, and the concentration of cyclophilin A protein in blood or the like.

CITATION LIST

Non Patent Literature

[NPL 1] Satoh K et al. Nat Med. 2009; 15 (6): pp 649-656.
[NPL 2] Satoh K et al. Circulation 2008; 117:3088-3098.
[NPL 3] Nigro P, Satoh K, et al. J Exp Med. 2011; 208: 53-66.
[NPL 4] Satoh K, et al. Antioxidants & Redox signaling 2010; 12:675-682.
[NPL 5] Satoh K, Shimokawa H, et al. Circ J 2010; 74:2249-2256.

SUMMARY OF INVENTION

Technical Problem

A primary object of the present invention is to provide a novel examination method for a cardiovascular disease.

Solution to Problem

The inventors of the present invention have made intensive studies to achieve the object, and as a result, have found that the cardiovascular disease can be examined by measuring the concentration of cyclophilin A protein in a sample, and determining the probability of development of the cardiovascular disease based on the measured concentration of cyclophilin A protein. The present invention has been accomplished by conducting additional studies based on such findings.

That is, the present invention encompasses embodiments of the invention according to the following items.

Item 1. An examination method for a cardiovascular disease, the examination method including the steps of: measuring a concentration of cyclophilin A protein in a human blood sample derived from a subject to be examined; and determining, based on the measured concentration of cyclophilin A protein, a probability of development of a cardiovascular disease in the subject to be examined.

Item 2. An examination method according to Item 1, in which the determination step includes determining that the probability of development of a cardiovascular disease in the subject to be examined is high when the measured concentration of cyclophilin A protein is equal to or higher than a preset cutoff value.

Item 2-1. An examination method according to Item 1, in which the determination step includes determining that the probability of development of a cardiovascular disease in the subject to be examined is high when the measured concentration of cyclophilin A protein is 15 ng/mL or more.

Item 3. An examination method according to Item 1, in which the determination step includes determining that the probability of development of a cardiovascular disease in the subject to be examined is high when the measured concentration of cyclophilin A protein is higher than a concentration of cyclophilin A protein obtained from a sample of a healthy subject.

Item 4. An examination method according to any one of Items 1 to 3, in which the sample includes plasma.

Item 5. An examination method according to any one of Items 1 to 4, in which the cardiovascular disease includes at least one kind selected from the group consisting of an ischemic heart disease, aortic aneurysm, and pulmonary hypertension.

Item 6. An examination kit for a cardiovascular disease, including means for measuring a concentration of cyclophilin A protein in a human blood sample.

Item 7. A treatment method for a cardiovascular disease, the treatment method including the steps of: measuring a concentration of cyclophilin A protein in a human blood sample derived from a subject to be examined; determining, based on the measured concentration of cyclophilin A protein, a probability of development of a cardiovascular disease in the subject to be examined; and subjecting the subject to be examined determined to have a high probability of development of the cardiovascular disease to a treatment for treating the cardiovascular disease and/or preventing progression of the cardiovascular disease.

Item 8. An examination method for an ischemic heart disease, the examination method including the steps of: measuring concentrations of cyclophilin A protein and cardiac troponin T protein in a human blood sample derived from a subject to be examined; and determining, based on the measured concentrations of cyclophilin A protein and cardiac troponin T protein, a probability of development of an ischemic heart disease in the subject to be examined.

Item 9. An examination method for an ischemic heart disease, the examination method including the steps of: measuring concentrations of cyclophilin A protein and C-reactive protein in a human blood sample derived from a subject to be examined; and determining, based on the measured concentrations of cyclophilin A protein and C-reactive protein, a probability of development of an ischemic heart disease in the subject to be examined.

Item 10. An examination method for pulmonary hypertension, the method including the steps of: measuring a concentration of cyclophilin A protein in a human blood sample derived from a subject to be examined and a tricuspid regurgitation pressure gradient (TRPG) of the subject to be examined; and determining, based on the measured concentration of cyclophilin A protein and TRPG, a probability of development of pulmonary hypertension in the subject to be examined.

Advantageous Effects of Invention

According to one embodiment of the present invention, the novel examination method for a cardiovascular disease is provided. The examination method according to the one embodiment of the invention of the present application can readily examine the cardiovascular disease with high accuracy and can distinguish a patient who requires a thorough examination or an appropriate treatment. Therefore, according to the examination method of the present invention, it is possible to more readily select a treatment suitable for an individual patient suspected to have the cardiovascular disease than ever before.

BRIEF DESCRIPTION OF DRAWINGS

FIG. 1 shows the distribution of ratios of patients (Patients (%)), i.e., patients with coronary artery stenosis (Patients with coronary stenosis) and patients without organic stenosis (Patients without organic stenosis) for the concentrations of cyclophilin A protein (CyPA level).

FIG. 2 are box-and-whisker plots showing correlations between CyPA levels and the severity of angiographic coronary artery disease. FIG. 2(A) is a box-and-whisker plot of CyPA levels in patients with organic stenosis (Stenosis) (stenosis in the intravascular lumen occupied 51% or more of the diameter) (N=189) and patients without organic stenosis (No stenosis) (N=131). The CyPA level was elevated in patients with coronary stenosis (P<0.001). FIG. 2(B) is a box-and-whisker plot of CyPA levels in patients without organic stenosis (No stenosis), patients with 1-vessel disease (1-VD), patients with 2-vessel disease (2-VD), or patients with 3-vessel disease (3-VD). CyPA levels were elevated in the patients with 1-VD, 2-VD, and 3-VD (all P<0.001) as compared to the control group (no stenosis). CyPA levels increased sequentially within the coronary stenosis group as the number of stenotic vessels increased (P value for trend<0.001).

FIG. 3 show correlations between quartiles of CyPA level and the numbers of stenotic coronary arteries and ratios of cases requiring cardiovascular intervention. The CyPA levels in the quartiles were as follows: 1st quartile (Q1): 6.1 ng/ml or less; 2nd quartile (Q2): 6.2 to 9.6 ng/ml; 3rd quartile (Q3): 9.7 to 17.4 ng/ml; 4th quartile (Q4): 17.5 ng/ml or more. FIG. 3(A) shows means of numbers of stenotic coronary arteries (Number of stenotic coronary arteries) in patients in quartiles of CyPA level (Quartiles of plasma Cyclophilin). CyPA levels were elevated in patients in 3rd quartile (Q3) (P<0.001) and 4th quartile (Q4) (P<0.001) as compared to 1st quartile (Q1). The number of stenotic coronary arteries in patients in the upper quartile (higher CyPA level) increased. FIG. 3(B) shows ratios of cases requiring cardiovascular intervention in patients in quartiles of CyPA level (Requirement for Cardiovascular Intervention (%)). The ratio of cases requiring cardiovascular intervention was higher in patients in 3rd quartile (Q3) (P<0.001) and patients in 4th quartile (Q4) (P<0.001) as compared to 1st quartile (Q1).

FIG. 4 are receiver-operating-characteristic curves (ROC curves) and c-statistic for CyPA level and determination of coronary organic stenosis and determination of requirement for cardiovascular intervention. The horizontal axis represents specificity, and the vertical axis represents sensitivity. In FIG. 4(A), the ROC curve represents the diagnostic performance of CyPA level to determine coronary organic stenosis by 50% or more in at least one vessel as compared to the reference standard of invasive quantitative coronary angiography (CAG). The c-statistic was 0.80 (95% confidence interval: 0.75 to 0.85). In FIG. 4(B), the ROC curve represents the diagnostic performance of CyPA level to determine the requirement for future cardiovascular intervention as compared to the reference standard of invasive quantitative coronary angiography (CAG). The c-statistic was 0.79 (95% confidence interval: 0.74 to 0.85).

FIG. 5 show correlations between the concentration of CyPA in plasma and risk factors of a cardiovascular disease. The concentration of CyPA in plasma significantly increased by the presence of risk factors including hypertension (Hypertension), diabetes (Diabetes), smoking (Smoking), dyslipidemia (Dyslipidemia), and advanced age of 68 years or older (Age (>68 yrs)). On the other hand, there was no variation depending on sex (Sex, female or male).

FIG. 6 shows CyPA levels and odds ratios (Odds Ratio) of a cardiovascular disease according to specific risk factors (Risk Factor). The logistic regression model was adjusted with age, sex, and body mass index (BMI) (Adjusted with Age, Sex, and BMI). Odds ratios for continuous variables are per 1-SD increase.

FIG. 7 shows changes in CyPA levels in a baseline period (Baseline) and a follow-up period (Follow-up). Number of patients treated: n=42, mean follow-up period: 273 days.

FIG. 8 show CyPA immunostaining images in a coronary artery sample obtained from a patient with acute myocardial infarction. High CyPA expression was observed just beneath the thin fibrous cap. FIG. 8(B) is an enlarged view of FIG. 8(A). Bars: 500 μm.

FIG. 9 are box-and-whisker plots showing correlations between CyPA levels (Plasma CyPA) and the presence or absence of aortic aneurysm diagnosed by angiography. FIG. 9(A) is a box-and-whisker plot of CyPA levels in patients with aortic aneurysm (Aortic Aneurysm) and control patients (Control) (without aortic aneurysm and cardiovascular disease (No Aneurysm, No CAD)). The CyPA level was elevated in patients with aortic aneurysm (P<0.001). FIG. 9(B) is a box-and-whisker plot of CyPA levels in patients without aortic aneurysm and coronary artery disease (No Aneurysm (-), No CAD (-)), patients with aortic aneurysm having a diameter of 55 mm or less (Aortic Aneurysms (<55 mm)), and patients with aortic aneurysm having a diameter of 55 mm or more (Aortic Aneurysms (>55 mm)).

FIG. 10 is a receiver-operating-characteristic curve (ROC curve) and a c-statistic for CyPA level and determination of coronary organic stenosis and determination of requirement for cardiovascular intervention. The horizontal axis represents specificity, and the vertical axis represents sensitivity. The c-statistic calculated from an area under the curve (ROC curve) (AUC) was 0.756.

FIG. 11 is a box-and-whisker plot showing a correlation between CyPA levels (Plasma CyPA) and the presence or absence of pulmonary hypertension. The plot is a box-and-whisker plot of CyPA levels in patients with pulmonary hypertension (PH) and control patients (Control). The CyPA level was elevated in patients with pulmonary hypertension (P<0.001).

FIG. 12 shows event-free survival ratios (Event-free survival ratio) in patients with pulmonary hypertension. The horizontal axis represents no event periods (No event period) by the number of days (days). The event-free survival ratio of a patient with a CyPA level of 22 ng/mL or more was significantly higher than that of a patient with a CyPA level of less than 22 ng/ml (P<0.001).

FIG. 13(A) shows reproducibility of CyPA level measurements. Across the entire patient group, duplicate measures of CyPA level (Plasma CyPA #1 and Plasma CyPA #2) were highly correlated (R=0.92). Depicted values reflect individual patients' absolute CyPA values divided by the measured value of a standard plasma pool run on the same plate. FIG. 13(B) is a dot plot showing CyPA levels and high-sensitivity CRP values in patients (n=320). There was no correlation between the CyPA levels and high-sensitivity CRP values.

FIG. 14 show correlations between the CyPA level and the severity of coronary artery disease that can be diagnosed by angiography in patients with higher high-sensitivity CRP value (high hsCRP) and patients with lower high-sensitivity CRP value (low hsCRP). FIG. 14(A) shows that in the patients with higher high-sensitivity CRP value (1 mg/L or more (hsCRP>1 m/L), n=141), the CyPA levels were elevated in patients with 1-vessel disease (1-VD), 2-vessel disease (2-VD), and 3-vessel disease (3-VD) as compared to patients without coronary stenosis (No stenosis) (all P<0.001). FIG. 14(B) shows that in patients with lower high-sensitivity CRP value (less than 1 mg/L, (hsCRP<1 mg/L), n=179), the CyPA level was elevated in patients with 1-vessel disease (1-VD) (P<0.001), 2-vessel disease (2-VD) (P<0.001), and 3-vessel disease (3-VD) (P<0.001) as compared to patients without coronary stenosis (No stenosis) (all P<0.001). In both the patient groups, the CyPA levels increased sequentially as the number of stenotic vessels increased.

FIG. 15 show correlations between quartiles of high-sensitivity CRP value (Quartile of plasma hsCRP) and the numbers of stenotic coronary arteries (Number of stenotic coronary arteries) and ratios of cases requiring cardiovascular intervention (Requirement for cardiovascular intervention (%)). FIG. 15(A) shows means of the numbers of stenotic coronary arteries inpatients in quartiles of high-sensitivity CRP value. There was no significant difference in the number of stenotic coronary arteries in patients in 4th quartile (Q4) as compared to 1st quartile (Q1) (P=0.107). FIG. 15(B) shows the ratios of cases requiring cardiovascular intervention (Requirement for Cardiovascular Intervention (%)) in patients in quartiles of high-sensitivity CRP value. There was no significant difference in the ratio of cases requiring cardiovascular intervention in patients in 4th quartile (Q4) compared to 1st quartile (Q1) (P=0.086). Cardiovascular intervention includes percutaneous coronary intervention (PCI) and coronary artery bypass grafting (CABG).

FIG. 16 show correlations between Gensini scores and quartiles of CyPA level and quartiles of high-sensitivity CRP value. FIG. 16(A) shows a correlation between quartiles of CyPA level and Gensini scores. FIG. 16(B) shows a correlation between quartiles of high-sensitivity CRP values and Gensini scores.

DESCRIPTION OF EMBODIMENTS

1. Examination Method for Cardiovascular Disease

The present invention provides an examination method for a cardiovascular disease. The cardiovascular disease to be examined by the examination method of the present invention is not particularly limited as long as the disease is one that develops in the heart and the vessel. Specific examples of the cardiovascular disease include diseases including: arteriosclerosis (such as atherosclerosis); angina caused by arteriosclerosis; an ischemic heart disease (also referred to as coronary artery disease) such as myocardial infarction; aortic aneurysm (such as thoracic aortic aneurysm or abdominal aortic aneurysm); cerebral infarction; and pulmonary arteriopathy such as pulmonary hypertension (pulmonary arterial hypertension). The arteriosclerosis and arteriosclerotic diseases are considered to develop and progress by inducing inflammation or thickening in the vessel wall with reactive oxygen species (ROS), which is produced in excess by various risk factors (such as smoking, dyslipidemia (hyperlipidemia), hypertension, diabetes, and aging) and acts as an oxidative stress, and are diseases associated with stenosis or occlusion of the vessel.

The term "examination" as used herein refers to examination of the presence or absence of a cardiovascular disease in a subject to be examined and examination of a risk of a cardiovascular disease. The "examination of a risk" includes an examination or determination of the presence or absence of a probability of development of a cardiovascular disease in the future. The term "examination" may be alternatively expressed as "determination".

The examination method of the present invention includes the steps of:

(i) measuring the concentration of cyclophilin A protein in a sample; and (ii) determining a probability of development of a cardiovascular disease based on the measured concentration of cyclophilin A protein.

First, the concentration of cyclophilin A protein in a sample is measured (Step (i)).

The sample is derived from a subject to be examined of the examination method of the present invention. A blood sample derived from a subject to be examined can be suitably used as the sample. The blood sample includes, for example, blood (whole blood), and serum and plasma derived from blood. In one preferred embodiment of the present invention, the sample is plasma.

Samples may be collected by a method known to a person skilled in the art. For example, blood may be collected by blood drawing using an injector or the like. It should be noted that blood drawing is desirably conducted by a healthcare professional such as a doctor or a nurse. Serum is obtained by removing hemocytes and specific blood clotting factors from blood, and, for example, may be obtained as a supernatant after blood clotting. Plasma is obtained by removing hemocytes from blood, and, for example, may be obtained as a supernatant after centrifugation of blood under a condition causing no blood clotting. The samples may be derived from the arteries, veins, or peripheral vessels of subjects to be examined.

The subject to be examined is not particularly limited, and examples thereof include mammals including humans. As mammals excluding the humans, there are given, for example, mice, rats, dogs, cats, cattle, sheep, and horses. The subject to be examined of the examination method of the present invention is preferably a human. When the subject to be examined is a human, the subject to be examined is particularly preferably a person suspected to have a cardiovascular disease, for example, a person having any subjective symptom such as chest pain or discomfort. The sex, age, and race of the subject to be examined are not particularly limited.

Cyclophilin A (CyPA) protein is encoded by peptidylprolyl isomerase A (PPIA) locus and encodes a chaperon protein that binds to cyclosporin. The structure of cyclophilin A protein is known. For example, the amino acid sequences of human cyclophilin A protein and mouse cyclophilin A protein were registered at GenBank provided by the National Center for Biotechnology Information (NCBI) under the following accession numbers (when a plurality of revisions have been registered, it is understood that each number refers to the latest revision):

Human cyclophilin A protein: NP_066953; and
Mouse cyclophilin A protein: NP_032933.

A previous study suggests that cyclophilin A protein promotes production of oxidative stress in models of abdominal aortic aneurysm, induced by angiotensin II in ApoE$^{-/-}$ mice, and is essential for generation of models of abdominal aortic aneurysm (Non Patent Literature 1). However, there is not known a correlation between the presence of an actual cardiovascular disease, in particular, a human cardiovascular disease, and the concentration of cyclophilin A protein in blood or the like.

Means for measuring the concentration of cyclophilin A protein in the sample is not particularly limited. It is possible to use, but not limited to, enzyme immunoassay (EIA), enzyme-linked immunosorbent assay (ELISA), western blotting, protein array, or the like.

To facilitate the measurement, the concentration of cyclophilin A protein in a sample may be measured using a commercially available kit. For example, human-derived cyclophilin A protein may be detected using Cyclophilin A ELISA Kit (product number: CSB-E09920H) manufactured by Cusabio Biotech Co., Ltd. (China), and mouse-derived cyclophilin A protein may be detected using Cyclophilin A ELISA Kit (product number: CSB-E09920M) manufactured by Cusabio Biotech Co., Ltd. The commercially available kits are preferably used according to protocols provided by the manufacturer, but the measurement method is not limited thereto.

The concentration of cyclophilin A protein to be measured may be a relative value to that of a control (the control may be set arbitrarily by a person skilled in the art) or an absolute amount represented by a weight per unit volume of a sample (for example, ng/ml). From the viewpoint of improving precision and accuracy of the examination method, the concentration of cyclophilin A protein to be measured is preferably an absolute amount.

Thus, the concentration of cyclophilin A protein in a sample is measured.

Subsequently, the probability of development of a cardiovascular disease is determined based on the measured concentration of cyclophilin A protein in the sample (Step (ii)).

In one embodiment of the present invention, when the measured concentration of cyclophilin A protein is higher than the concentration of cyclophilin A protein in a sample derived from a healthy subject, the subject to be examined is determined to have a probability of development of a cardiovascular disease. The concentration of cyclophilin A protein in the sample of a healthy subject can be appropriately measured by a person skilled in the art. The concentration may be generally from about 0 to 9 ng/ml, particularly from about 3 to 9 ng/ml.

In a preferred embodiment of the present invention, when the measured concentration of cyclophilin A protein in a sample is equal to or higher than a preset cutoff value, the subject to be examined can be determined to have a high probability of development of a cardiovascular disease. As described in Examples below, when the concentration of cyclophilin A protein is equal to or higher than a preset cutoff value, the subject to be examined significantly has a cardiovascular disease.

The cutoff value can be determined by various statistical analysis techniques. Examples of the cutoff value include a median or mean value of samples of patients with a cardiovascular disease, and a value determined based on ROC curve analysis. A plurality of cutoff values may be set.

In another embodiment of the present invention, in the case where the cardiovascular disease is an ischemic heart disease, when the concentration of cyclophilin A protein is about 15 ng/mL or more, preferably about 9.7 ng/mL or more, particularly preferably about 17.5 ng/ml or more, the subject to be examined can be determined to have a high probability of development of an ischemic heart disease. In a still another embodiment of the present invention, in the case where the cardiovascular disease is pulmonary hypertension, when the concentration of cyclophilin A protein is about 22 ng/mL or more, the patient can be determined to have a poor prognosis after treatment.

The examination method of the present invention may be combined with another known or future examination method for a cardiovascular disease. For example, the examination method may be combined with general means for examining a cardiovascular condition, such as measurement of blood pressure, measurement of heart rate, or recording of electrocardiogram.

In addition, for example, when the cardiovascular disease to be examined is an ischemic heart disease (coronary artery disease) (in particular, myocardial infarction), the examination method according to one embodiment of the present invention may be an examination method including a step of measuring the concentration of cardiac troponin T protein in a sample (cardiac troponin T test). Specific means of the cardiac troponin T test is known. In general, a sample is generally evaluated as positive when the concentration of cardiac troponin T protein in the sample is about 0.1 ng/mL or more, and the subject to be examined is determined to have a high probability of development of an ischemic heart disease. In the examination method according to such embodiment of the present invention, not only when the sample is evaluated as positive in the cardiac troponin T test, but also when the sample is evaluated as negative in the cardiac troponin T test and the concentration of cyclophilin A protein in the sample is higher than the concentration of cyclophilin A protein in a sample derived from a healthy subject, in particular, when the sample is evaluated as negative in the cardiac troponin T test and the measured concentration of cyclophilin A protein in the sample is equal to or higher than a preset cutoff value (for example, about 15 ng/mL or more), the subject to be examined can be determined to have a high probability of development of an ischemic heart disease.

When the cardiovascular disease to be examined is an ischemic heart disease (coronary artery disease) (in particular, myocardial infarction), the examination method according to another embodiment of the present invention may be an examination method including a step of measuring the concentration of C-reactive protein (CRP) in a sample. Means for measuring CRP is known. CRP is preferably measured by a high-sensitivity CRP (hsCRP) test, which can measure a low concentration of CRP. In general, when the high-sensitivity CRP value in a sample is 1 mg/L or more, the subject to be examined is determined to have a risk of development of or to have a probability of development of a cardiovascular disease such as myocardial infarction (for example, see the following literature: Ridker P M. Am Heart J 2004; 148: S19-S26.; Ridker P M, Cook N. Circulation 2004; 109: 1955-1959.). In the examination method according to such embodiment of the present invention, not only when the sample is evaluated as positive in the high-sensitivity CRP (hsCRP) test (typically, when the high-sensitivity CRP value is 1 mg/L or more), but also when the sample is evaluated as negative in the high-sensitivity CRP (hsCRP) test (typically, when the high-sensitivity CRP value is less than 1 mg/L) and the concentration of cyclophilin A protein in the sample is higher than the concentration of cyclophilin A protein in a sample derived from a healthy subject, in particular, when the high-sensitivity CRP value is evaluated as negative and the measured concentration of cyclophilin A protein in the sample is equal to or higher than a preset cutoff value (for example, about 15 ng/mL or more), the subject to be examined can be determined to have a risk of development of or to have a probability of development of a cardiovascular disease.

It should be noted that the structures of cardiac troponin T protein and C-reactive protein are known. For example, the amino acid sequences of human cardiac troponin T protein, mouse cardiac troponin T protein, human C-reactive protein, and C-reactive protein have been registered at GenBank provided by National Center for Biotechnology Information (NCBI) under the following accession numbers (when a plurality of revisions have been registered, it is understood that each number refers to the latest revision):

Human cardiac troponin T protein: NP_000355;
Mouse cardiac troponin T protein: NP_001123646;
Human C-reactive protein: NP_000558; and
Mouse C-reactive protein: NP_031794.

Further, when the cardiovascular disease to be examined is pulmonary hypertension, an examination method according to another embodiment of the present invention may be an examination method including a step of measuring a tricuspid regurgitation pressure gradient (TRPG) in a subject to be examined. The TRPG can be measured by cardiac ultrasonography. The TRPG refers to a difference between a pressure of blood pressed out of the heart and a pressure of blood having passed through the valve, and can be determined by echocardiography. In general, when the TRPG is about 50 mmHg or more, the subject to be examined is determined to have a high probability of development of pulmonary hypertension. In the examination method according to such embodiment of the present invention, not only when the TRPG is about 50 mmHg or more, but also when the TRPG is less than about 50 mmHg and the concentration of cyclophilin A protein in a sample is higher than that in a sample derived from a healthy subject, and when the TRPG is about 50 mmHg or less and the measured concentration of cyclophilin A protein in a sample is equal to or higher than a preset cutoff value (for example, about 15 ng/mL or more), the subject to be examined can be determined to have a high probability of development of pulmonary hypertension.

Thus, the probability of development of a cardiovascular disease is determined.

The subject to be examined determined to have a probability of development of a cardiovascular disease is preferably subjected to a thorough examination of the presence or absence of a cardiovascular disease and/or identification of a lesion by a thorough examination such as cardiac catheterization or angiography (including X-ray angiography, computed tomographic (CT) angiography, and magnetic resonance (MR) angiography).

Further, in particular, a patient determined to have a high probability of development of a cardiovascular disease by a thorough examination is preferably subjected to an appropriate treatment for treating and/or preventing progression of the cardiovascular disease. Examples of the appropriate treatment include, but not limited to, a medical treatment for suppressing progression of a cardiovascular disease by, for example, administration of a vasodilator, an antiplatelet agent, or the like; an intravascular treatment for expanding a stenotic vessel using a balloon or a stent (endovascular treatment); and a surgical treatment such as a surgery for removing a stenotic vessel or a surgery for introducing an alternative to a stenotic vessel (bypass surgery, introduction of synthetic blood vessel, graft of autogenous vessel, or the like). When the cardiovascular disease is an ischemic heart disease (coronary artery disease), preferred examples thereof include percutaneous coronary intervention (PCI) and coronary artery bypass grafting (CABG). In addition, there may be conducted a guidance or medical measure for reducing risk factors of a cardiovascular disease, such as smoking, dyslipidemia (hyperlipidemia), hypertension, and diabetes.

The subject to be examined determined to have a low probability of development of a cardiovascular disease is preferably subjected to appropriate follow-up and treated depending on the progression of the disease.

2. Kit

The present invention also provides an examination kit for a cardiovascular disease, including means for measuring the concentration of cyclophilin A protein in a sample.

Examples of the means for measuring the concentration of cyclophilin A protein in a sample include, but not limited to, means for measuring the concentration of cyclophilin A protein in a sample by the above-mentioned means such as EIA, ELISA, Western-blotting, or protein array.

For example, the means for measuring the concentration of cyclophilin A protein in a sample, included in the kit of the present invention, is preferably means capable of evaluating whether the measured concentration of cyclophilin A protein is higher or lower than the concentration of cyclophilin A protein in a sample derived from a healthy subject or means capable of evaluating whether or not the measured concentration of cyclophilin A protein in a sample is 15 ng/mL or more. The means is particularly preferably the means capable of evaluating whether or not the measured concentration of cyclophilin A protein in a sample is 15 ng/mL or more.

In addition, the kit of the present invention may include another component, if necessary. Examples of the other component include, but not limited to, an instrument for collecting a sample (for example, injector), a positive control sample, and a negative control sample. The kit may further include a leaflet showing procedures of the examination method.

The kit may further include means for measuring a biomarker for a cardiovascular disease, excluding cyclophilin A protein. For example, when the cardiovascular disease to be examined by the kit of the present invention is an ischemic heart disease (coronary artery disease) (in particular, myocardial infarction), the kit according to one embodiment of the present invention may be a kit including means for measuring the concentration of cardiac troponin T protein in a sample. The means is preferably means capable of evaluating whether or not the concentration of cardiac troponin T protein in a sample is 1 mg/L or more.

When the cardiovascular disease to be examined by the kit of the present invention is an ischemic heart disease (coronary artery disease) (in particular, myocardial infarction), the kit according to one embodiment of the present invention may be a kit including means for measuring the concentration of C-reactive protein (CRP) in a sample. The means is preferably means capable of conducting high-sensitivity CRP (hsCRP) test, which can measure even a low concentration of CRP. In addition, the means is preferably means capable of evaluating whether or not the concentration of C-reactive protein in a sample is 1 mg/L or more.

The kit of the present invention can be created according to a conventional method by adding the above-mentioned components, if necessary.

The usage of the kit is not particularly limited, and the kit is preferably used in the examination method described above. When the kit is used in the examination method described above, the examination can easily be conducted.

3. Treatment Method

The present invention also provides a treatment method for a cardiovascular disease. The term "treatment" as used herein refers to a treatment for a cardiovascular disease and maintenance therapy for symptomatic relief and recurrence prevention.

The treatment method of the present invention includes the steps of:

(i) measuring the concentration of cyclophilin A protein in a human blood sample;

(ii) determining, based on the measured concentration of cyclophilin A protein, the probability of development of a cardiovascular disease in a subject to be examined from which the sample is derived; and (iii) subjecting a subject to be examined determined to have a high probability of development of the cardiovascular disease to a treatment for treating the cardiovascular disease and/or preventing progression of the cardiovascular disease.

In Steps (i) and (ii), the measurement step and determination step described in the above-mentioned section "1." are conducted.

Subsequently, the subject to be examined determined to have a high probability of development of a cardiovascular disease is subjected to a treatment for treating the cardiovascular disease and/or preventing progression of the cardiovascular disease (Step (iii)). In the period between Steps (ii) and (iii), there may be conducted a thorough examination of the presence or absence of a cardiovascular disease and/or identification of a lesion by a thorough examination such as cardiac catheterization or angiography (including X-ray angiography, computed tomographic (CT) angiography, and nuclear magnetic resonance (MR) angiography).

Examples of the treatment for treating a cardiovascular disease and/or preventing progression of a cardiovascular disease include, but not limited to: a medical treatment for suppressing progression of a cardiovascular disease by, for example, administration of a vasodilator, an antiplatelet agent, or the like; an intravascular treatment for expanding a stenotic vessel using a balloon or a stent (endovascular treatment); and a surgical treatment such as a surgery for removing a stenotic vessel or a surgery for introducing an alternative to a stenotic vessel (bypass surgery, introduction of synthetic blood vessel, graft of autogenous blood vessel, or the like). When the cardiovascular disease is an ischemic heart disease (coronary artery disease), preferred examples thereof include percutaneous coronary intervention (PCI) and coronary artery bypass grafting (CABG). In addition, there may be conducted a guidance or medical measure for reducing risk factors of a cardiovascular disease, such as smoking, dyslipidemia (hyperlipidemia), hypertension, and diabetes.

Thus, the cardiovascular disease is treated.

EXAMPLES

The present invention is hereinafter described in more detail by way of Examples and the like. However, the present invention is not limited thereto.

Example 1

The correlation between coronary artery disease and the concentration of cyclophilin A protein in plasma was examined.

1. Method

Patient Groups

A prospective observational study of the prognostic value of CyPA was conducted in patients with symptoms or signs of coronary artery disease (CAD) who were referred to the Tohoku University Hospital (Sendai) for selective coronary angiography (CAG) from November 2007 through October 2011. It should be noted that, if patients underwent angiography more than once, an analysis was based only on data obtained at the time of the first angiographic study. Patients with valvular or congenital heart disease and patients with unstable angina or myocardial infarction were excluded. 320 patients who had angina pectoris and signs of ischemia on exercise electrocardiogram or myocardial radionuclide imaging were enrolled. The Ethical Review Board approved the study, and written informed consent was given by all participating patients.

Coronary Angiography

In the observation period (baseline period), a selective coronary angiography test was conducted with measurement results on the angiographic data system. Two cardiologists, who were blinded to the patients' CyPA plasma levels, evaluated the angiograms. The degree of coronary stenosis was evaluated according to the American Heart Association standards. Narrowing of the intravascular lumen by 51% or more of the diameter was considered to indicate clinically significant stenosis. The patients were classified according to the severity of CAD as a group of patients having no clinically significant organic stenosis, or groups of 1-, 2-, and 3-vessel disease (VD). The left anterior descending coronary artery, left circumflex coronary artery, and right coronary artery were observed to evaluate the number of stenotic coronary arteries as 0 to 3-VD. Stenosis of the left main coronary artery was evaluated as 2-VD. The correlation between the plasma CyPA level and the number of stenotic coronary arteries was analyzed to evaluate the severity of CAD.

Immunostaining

CyPA immunostaining was conducted according to a known technology (Jin Z G et al., Arterioscler Thromb Vasc Biol. 2004; 24: 1186-1191; Suzuki J et al., Circ Res. 2006; 98: 811-817; Satoh K et al., Circulation. 2008; 117: 3088-3098). Specifically, paraformaldehyde-fixed frozen sections were incubated overnight at 4° C. with a primary antibody (anti-human CyPA polyclonal antibody, 1:1,000 dilution; manufactured by BIOMOL Research Laboratories). Subsequently, peroxidase-conjugated streptavidin (1:1,000 dilution; manufactured by Jackson ImmunoResearch Laboratories, product number 016-030-084) and NovaRed substrate kit (manufactured by Vector Laboratories, product number SK-4800) were used. The samples were counterstained with hematoxylin. As a negative control, a non-specific IgG was used in place of the primary antibody.

Baseline Measurements

Baseline measurement values were obtained from the database of the Department of Cardiovascular Medicine at the Tohoku University by means of a computerized search conducted on Dec. 7, 2011. No patients were lost to follow-up.

All patients had a recorded medical history that included any previous myocardial infarction, previous revascularization, angina pectoris, hypertension, stroke or transient ischemic attacks, diabetes, and smoking status. The cardiovascular risk factor was evaluated in terms of hypertension, diabetes, smoking, aging, and dyslipidemia. Patients with hypertension were evaluated as being at risk if their blood pressure was 140/90 mmHg or more or they had a history of antihypertensive drug use. Patients with diabetes were evaluated as being at risk if their fasting glucose level was 126 mg/dl or more or they had a history of hypoglycemic drug or insulin use. Patients with dyslipidemia were evaluated as being at risk if their LDL cholesterol was 140 mg/dl or more or they were taking a lipid-lowering drug.

Before CAG, fasting blood samples were drawn from the antecubital vein of the patients who were resting supine. Plasma samples were collected using EDTA and centrifuged for 10 minutes at 2,500 g within 30 minutes of collection, and aliquots were stored at −80° C.

CyPA levels were measured with use of an immunoassay based on the sandwich technique using Human Cyclophilin A ELISA Kit (manufacture by Cusabio Biotech, product number CSB-E09920H) according to the protocol provided by the manufacturer. The detection limit was 0.78 ng/ml. Across the entire analysis, duplicate measures of the CyPA level were highly correlated (R=0.92).

The high-sensitivity CRP (hsCRP) was measured based on a sandwich technique (Roche Diagnostics K.K.). Other measurement values were determined from samples subjected to measurement using an autoanalyzer.

Statistical Analysis

Baseline characteristics of the study patients, grouped according to CyPA levels, are presented as frequencies and percentages, and continuous variables as means and standard deviations, or medians and interquartile ranges for variables with skewed distributions. Baseline characteristics were compared among quartiles with use of the chi square test for discrete variables and the Wilcoxon or Kruskal-Wallis rank-sum test for continuous variables.

Additional CyPA analyses were conducted in subgroups defined according to the results of angiography. A Student's t-test was used for comparisons between 2 groups. Dunnett's multiple comparison of means was used for multi-group comparison after analysis of variance (ANOVA). Receiver-operating-characteristic (ROC) curves were constructed to evaluate the sensitivity and specificity of plasma CyPA measurements obtained before CAG and to compare the ability to determine the presence and severity of CAD.

Logistic regression analyses were used to estimate the association between CyPA levels and CAD status after adjustment for age, sex, smoking status, presence or absence of diabetes, presence or absence of hypertension, and LDL cholesterol level. Adjusted odds ratios were determined both for CyPA levels of 15 ng/ml or more and across quartiles. Model performance was evaluated according to discrimination, by means of the area under the ROC curve (c-statistic), and calibration, as indicated by the Hosmer-Lemeshow goodness-of-fit test. The analyses were conducted with CyPA levels as a categorical variable with the lowest quartile serving as reference for the other 3 quartiles. Determined P values are 2-tailed P values, and P values of 0.05 or less indicate statistical significance. Statistical analyses were conducted with SPSS, version 19.0 (Chicago, Ill., US) and JMP, version 9.02 (Cary, N.C., US).

2. Results and Discussion

FIG. 1 shows the distribution of patients with and without coronary stenosis for the concentrations of cyclophilin A (CyPA) protein in plasma (hereinafter sometimes simply referred to as "CyPA level"). The CyPA levels in patients with coronary interstitial stenosis were significantly higher than those in patients without stenosis.

FIG. 2 show correlations between the CyPA levels and the severity of angiographic coronary artery disease. The CyPA level increased with the severity of angiographic coronary artery disease (p<0.001).

All the cases were divided into four groups based on the concentration of CyPA in plasma to evaluate the correlation between the number of stenotic coronary arteries and the concentration of CyPA in plasma. Table 1 shows the patients' clinical background and laboratory data according to the quartiles of CyPA. Patients with CyPA in the upper quartile (high plasma levels of CyPA) were older and were more likely to have clinically significant coronary artery disease (p<0.001). The prevalence of both hypertension and diabetes was higher in the 4th quartile, and these patients showed a slightly reduced estimated glomerular filtration rate (eGFR).

demonstrate that the level of CyPA is useful for the determination of coronary organic stenosis (c-statistic=0.802) and the requirement for cardiovascular intervention (c-statistic=0.793).

FIG. 5 show correlations between the CyPA levels and cardiovascular risk factors. The CyPA levels were elevated in patients with traditional cardiovascular risk factors such as hypertension, diabetes, smoking, hyperlipidemia, and advanced age (68 years or older) (all P<0.001).

Division of the cohort according to CyPA level provided additional evidence of a correlation between the CyPA level

TABLE 1

| Table 1. Baseline Clinical Characteristics According to Quartiles of CyPA.* | | | | | |
|---|---|---|---|---|---|
| | 1st Quartile (N = 80) | 2nd Quartile (N = 80) | 3rd Quartile (N = 80) | 4th Quartile (N = 80) | P value |
| CyPA level (ng/ml) | 0.0-6.1 | 6.2-9.6 | 9.7-17.4 | 17.5-50.9 | |
| Age (yr) | | | | | <0.001 |
| Median | 58 | 63 | 68 | 68 | |
| Interquartile range | 50-68 | 55-71 | 60-75 | 60-74 | |
| Male sex (%) | 60 | 61 | 66 | 76 | 0.122 |
| Family history of ischemic heart disease (%) | 11 | 18 | 4 | 10 | 0.046 |
| Medical history (%) | | | | | |
| Hypertension | 56 | 59 | 75 | 88 | <0.001 |
| Diabetes | 36 | 34 | 48 | 55 | 0.022 |
| Dyslipidemia | 51 | 51 | 70 | 80 | <0.001 |
| Current smoker (%) | 28 | 34 | 49 | 59 | <0.001 |
| Angiographic findings (%) | | | | | <0.001 |
| No coronary artery stenosis | 71 | 61 | 20 | 13 | |
| 1-vessel disease | 23 | 31 | 41 | 29 | |
| 2-vessel disease | 3 | 4 | 24 | 31 | |
| 3-vessel disease | 4 | 4 | 11 | 28 | |
| Requirement for PCI or CABG during follow up period (%) | 8 | 8 | 23 | 40 | 0.019 |
| Body-mass index# | | | | | 0.003 |
| Median | 25 | 24 | 24 | 23 | |
| Interquartile range | 23-27 | 22-26 | 21-26 | 21-25 | |
| eGFR (ml/min/1.73 m$^2$) | 54 ± 17 | 59 ± 19 | 51 ± 20 | 49 ± 19 | <0.001 |
| Left ventricular ejection fraction - % | 65 ± 10 | 66 ± 8 | 59 ± 12 | 63 ± 12 | 0.090 |
| Lipid Status (mg/dL) | | | | | |
| LDL cholesterol | 105 ± 36 | 105 ± 29 | 96 ± 35 | 97 ± 33 | 0.078 |
| HDL cholesterol | 47 ± 13 | 49 ± 12 | 49 ± 12 | 49 ± 14 | 0.837 |
| Triglycerides | 127 ± 69 | 147 ± 95 | 130 ± 73 | 132 ± 100 | 0.576 |
| Hemoglobin A1c | 6.4 ± 1.4 | 6.3 ± 0.8 | 6.4 ± 0.9 | 6.6 ± 1.2 | 0.067 |
| High-sensitive CRP (mg/L) | 2.3 ± 3.2 | 1.7 ± 2.6 | 2.3 ± 3.1 | 1.8 ± 2.8 | 0.103 |
| Medication (%) | | | | | |
| Aspirin | 16 | 30 | 51 | 71 | <0.001 |
| β-blocker | 25 | 29 | 46 | 55 | <0.001 |
| Statin | 39 | 35 | 56 | 70 | <0.001 |
| ACE inhibitor | 28 | 24 | 31 | 39 | 0.212 |
| ARB | 24 | 26 | 28 | 33 | 0.654 |
| Ca blocker | 51 | 55 | 61 | 58 | 0.550 |

*Plus-minus values are means + SD. ACE denotes angiotensin-converting enzyme, ARB angiotensin-receptor blocker.
The body-mass index is the weight in kilograms divided by the square of the height in meters.

FIG. 3 show correlations between quartiles of CyPA level and the numbers of stenotic coronary arteries and ratios of cases requiring cardiovascular intervention. The number of stenotic coronary arteries was significantly increased in patients with CyPA in the upper quartile (high levels of CyPA) (P<0.001). Further, the ratios of cases requiring cardiovascular intervention, such as percutaneous coronary intervention (PCI) and coronary artery bypass grafting (CABG) (Requirement for PCI or CABG during follow up period (%)), were significantly higher in the 4th quartile as compared to the lower quartiles.

The ROC curves and c-statistic were calculated based on the CyPA levels. FIG. 4 show the results. The ROC curves and CAD. In the logistic regression analysis adjusted for age, sex, and traditional cardiovascular risk factors (smoking status, presence or absence of diabetes, presence or absence of hypertension, presence or absence of dyslipidemia), quartiles 2, 3, and 4 were correlated with an increased risk of CAD as compared to the quartile of lowest CyPA level (odds ratio: 1.73, 9.94, and 10.29; P-value for trend<0.001). This result remained significant after adjustment for traditional cardiovascular risk factors and high-sensitivity CRP value (Adjusted for Cardiovascular Risk Factors and hsCRP) (odds ratio: 1.84, 10.53, and 10.78; P-value for trend<0.001). Table 2 shows the results.

TABLE 2

Table 2. Coronary Artery Disease Status According to Quartiles of plasma CyPA.

| Variable | No. of Patients | Odds Ratio for Coronary Artery Disease (95% CI)* | |
|---|---|---|---|
| | | Adjusted for Cardiovascular Risk Factors | Adjusted for Cardiovascular Risk Factors and hsCRP |
| Quartile 1 | 80 | 1.00 | 1.00 |
| Quartile 2 | 80 | 1.73 (0.78-3.85) | 1.84 (0.82-4.14) |
| Quartile 3 | 80 | 9.94 (3.98-24.83) | 10.53 (4.16-26.63) |
| Quartile 4 | 80 | 10.29 (3.95-26.79) | 10.78 (4.13-28.14) |
| P value for trend | | P < 0.001 | P < 0.001 |

*Cardiovascular risk factors included in the logistic-regression model were age, sex, smoking status, presence or absence of diabetes, presence or absence of hypertension, and presence or absence of dyslipidemia.

FIG. 6 shows odds ratios determined from CyPA levels and logistic regression models of known cardiovascular risk factors. Several known cardiovascular risk factors were correlated with CAD in logistic regression models adjusted for age, sex, and body mass index (BMI). Diabetes and hypertension were each correlated with an increased risk of CAD. Each of the known risk factors, and CyPA levels were included in a univariable logistic regression analysis. In this model, which included the high-sensitivity CRP value, a CyPA level of 15 ng/ml or more remained significantly correlated with cardiovascular disease status (odds ratio=6.20, P<0.001).

Further, multivariable analysis demonstrated that, in addition to the known risk factors (age, sex, smoking, hypertension, diabetes, and hsCRP), a CyPA level of 15 ng/ml or more was significantly correlated with cardiovascular disease status (Table 3).

TABLE 3

Table 3. Correlated Risk Factors for Coronary Stenosis

| | Univariable Analysis | | | Multivariable Analysis* | | |
|---|---|---|---|---|---|---|
| | Odds Ratio | 95% CI | P value | Odds Ratio | 95% CI | P value |
| Age | 1.08 | 1.05-1.10 | <0.001 | 1.07 | 1.04-1.10 | <0.001 |
| Men | 1.76 | 1.10-2.82 | 0.018 | 1.58 | 0.81-3.09 | 0.184 |
| BMI | 0.95 | 0.89-1.01 | 0.085 | | | |
| Hypertension | 5.34 | 3.19-8.93 | <0.001 | 1.85 | 0.95-3.63 | 0.073 |
| Smoking | 2.44 | 1.52-3.90 | <0.001 | 1.82 | 0.95-3.49 | 0.072 |
| Dyslipidemia | 4.03 | 2.49-6.51 | <0.001 | 2.37 | 1.23-4.55 | 0.010 |
| Diabetes | 5.87 | 3.50-9.86 | <0.001 | 4.71 | 2.53-8.78 | <0.001 |
| Family history of IHD | 0.663 | 0.33-1.35 | 0.258 | | | |
| CyPA > 15 ng/mL | 7.58 | 4.00-14.38 | <0.001 | 4.14 | 2.00-8.57 | <0.001 |
| hsCRP > 1 mg/L | 1.77 | 1.12-2.79 | 0.014 | 1.58 | 0.87-2.86 | 0.135 |

CI indicates confidence interval; BMI, body-mass index; IHD, ischemic heart disease; CyPA, cyclophilin A; hsCRP, high-sensitive CRP.
*Analysis was performed on 8 variables including age, sex, hypertension, smoking, dyslipidemia, diabetes mellitus, CyPA > 15 ng/mL and hsCRP > 1 mg/L.

The inclusion of CyPA level resulted in significant improvement of the overall performance of the logistic regression model. The c-statistic increased from 0.807 to 0.870 when the CyPA level was added to known cardiovascular risk factors (age, sex, smoking, hypertension, diabetes, and dyslipidemia). When the high-sensitivity CRP value was included in the baseline model, the c-statistic increased from 0.807 to 0.873. The inclusion of CyPA level did not reduce model discrimination in the evaluation using the goodness-of-fit test. That is, the CyPA level adds information above and beyond that provided by sex, family history with respect to ischemic heart disease, presence or absence of hypertension and diabetes, smoking status, body mass index (BMI), eGFR, and plasma lipid level.

Excluding the 141 patients with positive high-sensitivity CRP values (plasma level: 1 mg/L or more) did not significantly change the results. In patients with high-sensitivity CRP values of less than 1 mg/L, the adjusted odds ratio for CAD of patients in the 4th quartile of CyPA level, as compared to that of patients in the 1st quartile, was 13.2 (95% confidence interval: 3.2 to 53.9, P<0.001). In addition, a CyPA level of 15 ng/ml or more remained as a strong prognostic marker, with an adjusted odds ratio of 5.9 (95% confidence interval: 2.3 to 14.8, P<0.001). Among patients with high-sensitivity CRP values of 1.000 or more, the same trend was observed, suggesting the usefulness of combining these biomarkers for predicting CAD.

Levels of CyPA as Biomarker for Determining Therapeutic Outcome

The CyPA level increased according to the atherosclerotic risk factors such as sex, hypertension, diabetes, dyslipidemia, and smoking (FIG. 6). All of the risk factors are oxidative stress inducers. Therefore, there was examined usefulness of the CyPA level as a biomarker of therapeutic outcome after controlling risk factors.

A follow-up study after the addition of drugs to control risk factors was conducted. After treatment in patients (n=42), a comparison between the samples obtained in baseline and follow-up periods (mean follow-up period: 273 days) revealed a significant reduction of the CyPA level after treatment (p=0.003). FIG. 7 shows the results. That is, the treatments that control atherosclerotic risk factors decreased CyPA levels in patients with coronary artery disease, suggesting that the CyPA levels are useful for the evaluation of systemic oxidative stress and the therapeutic effect of medication.

CyPA and Atherosclerotic Unstable Plaque

Accumulation of CyPA in atherosclerotic plaque of coronary arteries was observed. FIG. 8 show the results. Strong CyPA expression was observed in coronary arteries in patients with myocardial infarction. In particular, the high expression of CyPA was observed just beneath the thin fibrous cap of atherosclerotic plaque. This suggests that CyPA secreted is accumulated in atherosclerotic plaque of coronary arteries.

Example 2

A correlation among aortic aneurysm and the concentration of cyclophilin A protein in plasma was examined.

1. Method

Patient Groups

Among the patients examined in Example 1, patients determined to have thoracic aortic aneurysm or abdominal aortic aneurysm by diagnostic imaging were classified into a group of patients with aortic aneurysm (N=60). Among the patients examined in Example 1, patients determined to have no thoracic aortic aneurysm and no abdominal aortic aneurysm were classified into a control group (N=69).

Statistical Analysis

A statistical analysis was conducted according to the method described in Example 1.

2. Results and Discussion

FIG. 9 show correlations between CyPA level and the presence or absence of aortic aneurysm that can be discriminated by diagnostic imaging such as CT. The CyPA level was significantly higher in the patients with aortic aneurysm (p<0.001). The CyPA level tended to be particularly higher in the patients with aortic aneurysm with a diameter of 55 mm or more for whom the necessity for surgery was determined to be high.

A ROC curve and c-statistic for determination of aortic aneurysm were calculated based on CyPA level. FIG. 10 shows the results. The ROC curve suggests that the CyPA level is useful for determination of aortic aneurysm (c-statistic=0.756).

Example 3

A correlation among pulmonary hypertension and the concentration of cyclophilin A protein in plasma was examined.

1. Method

Patient Groups

This study was conducted using plasma samples obtained from patients with pulmonary hypertension (N=130) and control patients (N=25) in right heart catheterization, which was conducted at the Tohoku University Hospital (Sendai) from 2008 through 2011. The control patients are ones who were suspected to have pulmonary hypertension in echocardiography but were found to have no pulmonary hypertension in right heart catheterization (mean pulmonary artery pressure (mPAP)<25 mmHg).

Baseline Measurement and Statistical Analysis

Baseline Measurement and a statistical analysis were conducted according to the methods described in Example 1.

2. Results and Discussion

FIG. 11 shows a correlation between CyPA level and the presence or absence of pulmonary hypertension. The CyPA level was significantly higher in the patients with pulmonary hypertension (p<0.001).

FIG. 12 shows event-free survival ratios in patients having a CyPA level of 22 ng/mL or more and patients having a CyPA level of less than 22 ng/ml, in the baseline period. In the patients having a CyPA level of 22 ng/mL or more, event-free survival ratios were significantly higher than those of the patients having a CyPA level of less than 22 ng/ml (P<0.001).

The results suggest that the CyPA level is useful as a biomarker for evaluation of the therapeutic effect of pulmonary hypertension and for determination of prognosis.

Example 4

The correlation between the concentration of cyclophilin A protein in plasma and high-sensitivity CRP value (hsCRP value) was evaluated.

1. Method

Patient Groups

The same patient groups as those of Example 1 were evaluated.

Measurement Method, Baseline Measurement, and Statistical Analysis

A measurement method, baseline measurement, and a statistical analysis were conducted according to the methods described in Example 1. The Gensini score was calculated according to the method described in the following literature: Gensini G G. Am J Cardiol 1983; 51: 606.

2. Results and Discussion

FIG. 13 show the results. FIG. 13A shows reproducibility of CyPA level measurements in duplicates. FIG. 13B is a dot plot showing CyPA level and high-sensitivity CRP value in patients (n=320). As apparent from FIG. 13B, there was no correlation between the CyPA level and high-sensitivity CRP value.

Table 4 shows the patients' clinical backgrounds and values of laboratory parameters according to high-sensitivity CRP value and the presence or absence of coronary artery disease (CAD). The patients with higher high-sensitivity CRP values (1 mg/L or more, n=141; i.e., "positive") and those with lower high-sensitivity CRP values (less than 1 mg/L, n=179; i.e., "negative") did not show a significant difference in the CyPA levels (P=0.511). Further, there was no significant difference between the two patient groups in their angiographic findings (P=0.602) and ratios of patients requiring cardiovascular intervention (Requirement for PCI or CABG during follow up period (%)) (P=0.348).

TABLE 4

Table S1. Baseline Clinical Characteristics According to the hsCRP Levels and the Presence or Absence of Clinically Significant CAD*

|  | hsCRP ≥ 1 mg/L | | | hsCRP < 1 mg/L | | |
| --- | --- | --- | --- | --- | --- | --- |
|  | No CAD (n = 47) | CAD (n = 94) | P value | No CAD (n = 84) | CAD (n = 95) | P value |
| Age (years) |  |  | <0.001 |  |  | <0.001 |
| Median | 59 | 69 |  | 57 | 69 |  |
| Interquartile range | 52-66 | 62-75 |  | 50-64 | 62-76 |  |
| Male sex (%) | 62 | 70 | 0.333 | 56 | 73 | 0.020 |
| Family history of IHD (%) | 9 | 3 | 0.173 | 15 | 15 | 0.891 |
| Medical history (%) |  |  |  |  |  |  |
| Hypertension | 64 | 83 | 0.011 | 40 | 84 | <0.001 |
| Diabetes | 21 | 65 | <0.001 | 19 | 54 | <0.001 |
| Dyslipidemia | 45 | 70 | 0.003 | 44 | 82 | <0.001 |
| Current smoker (%) | 28 | 56 | 0.001 | 31 | 45 | 0.050 |

TABLE 4-continued

Table S1. Baseline Clinical Characteristics According to the hsCRP Levels and the Presence or Absence of Clinically Significant CAD*

| | hsCRP ≥ 1 mg/L | | | hsCRP < 1 mg/L | | |
|---|---|---|---|---|---|---|
| | No CAD (n = 47) | CAD (n = 94) | P value | No CAD (n = 84) | CAD (n = 95) | P value |
| Angiographic findings (%) | | | | | | 0.602# |
| No coronary artery stenosis | 100 | 0 | | 100 | 0 | |
| 1-vessel disease | 0 | 50 | | 0 | 58 | |
| 2-vessel disease | 0 | 31 | | 0 | 22 | |
| 3-vessel disease | 0 | 19 | | 0 | 20 | |
| Requirement for PCI or CABG during follow up period (%) | 0 | 47 | | 0 | 40 | 0.348# |
| BMI | | | 0.957 | | | 0.007 |
| Median | 24 | 24 | | 24 | 23 | |
| Interquartile range | 22-26 | 22-26 | | 21-26 | 22-26 | |
| eGFR (ml · min$^{-1}$ · 1.73 m$^{-2}$) | | | 0.005 | | | <0.001 |
| Median | 58 | 49 | | 66 | 51 | |
| Interquartile range | 48-68 | 40-60 | | 53-79 | 42-63 | |
| Left ventricular ejection fraction (%) | | | <0.001 | | | 0.001 |
| ≥60 | 96 | 84 | | 93 | 81 | |
| <60 | 4 | 16 | | 7 | 19 | |
| Lipid Status (mg/dl) | | | | | | |
| LDL cholesterol | 119 ± 41 | 100 ± 33 | 0.017 | 110 ± 25 | 90 ± 33 | <0.001 |
| HDL cholesterol | 42 ± 10 | 45 ± 12 | 0.192 | 53 ± 13 | 51 ± 13 | 0.356 |
| Triglycerides | 134 ± 64 | 131 ± 88 | 0.886 | 137 ± 85 | 135 ± 92 | 0.853 |
| Hemoglobin A$_{1C}$ | 6.1 ± 0.7 | 6.8 ± 1.4 | 0.017 | 6.0 ± 0.8 | 6.5 ± 0.9 | 0.002 |
| CyPA (ng/ml) | | | | | | 0.511# |
| | 8.0 ± 7.9 | 16.1 ± 10.1 | <0.001 | 7.7 ± 5.2 | 17.1 ± 10.0 | <0.001 |

*Plus-minus values are means ± SD.
P value is for the comparison between the groups with lower hsCRP and those with higher hsCRP.
BMI, body-mass index; CABG, coronary artery bypass grafting; CAD, coronary artery disease; CyPA, cyclophilin A; eGFR, estimated glomerular filtration rate; HDL, high-density lipoprotein; hsCRP, high-sensitivity C-reactive protein; IHD, ischemic heart disease; LDL, low-density lipoprotein; PCI, percutaneous coronary intervention.

FIG. 14 show correlations between CyPA level and the severity of coronary artery disease that can be discriminated by angiography in patients with higher high-sensitivity CRP values and patients with lower high-sensitivity CRP values. In both the two patient groups, the CyPA level was correlated with the severity of coronary artery disease (CAD). In both the group of patients with higher high-sensitivity CRP values and the group of patients with lower high-sensitivity CRP values, the CyPA level was higher in the patients with severe CAD.

FIG. 15 show correlations between quartiles of high-sensitivity CRP value and the numbers of stenotic coronary arteries and ratios of cases requiring cardiovascular intervention. The number of stenotic coronary arteries slightly increased in the 4th quartile of high-sensitivity CRP value. However, the significance represented by the P-value (P=0.107) was small compared to the 4th quartile of CyPA level (P<0.001, FIG. 3A). Moreover, the quartiles of high-sensitivity CRP value did not show a strong correlation with the requirement for future cardiovascular intervention.

FIG. 16 show correlations of Gensini scores for quartiles of CyPA level and quartiles of high-sensitivity CRP value. The Gensini score significantly increased in the 4th quartile of CyPA level (P<0.001, FIG. 16A). The Gensini score significantly increased in the 4th quartile of high-sensitivity CRP value (P=0.007, FIG. 16B). The CyPA level was superior to the high-sensitivity CRP value as an indicator for evaluation of the severity of coronary atherosclerosis.

It should be noted that the Gensini score indicates the severity of CAD (see, for example, the following literatures: Ozaki Y, Imanishi T, Taruya A, Aoki H, Masuno T, Shiono Y, et al. Circ J2012; 76: 2412-2418, and Gensini G G. Am J Cardiol 1983; 51: 606.).

Among the 179 patients with low high-sensitivity CRP values, 95 (53.1%) had CAD (Table 4). Among these patients, the median CyPA level for patients with CAD (17.1 ng/ml) was significantly elevated (P<0.001) as compared to that for patients without CAD (7.7 ng/ml). Among the 141 patients with high high-sensitivity CRP values, 94 (66.7%) had CAD (Table 4). Among these patients, the median CyPA level for patients with CAD (16.1 ng/ml) was significantly elevated (P<0.001) as compared to that for patients without CAD (8.0 ng/ml). On the other hand, the quartiles of CyPA level did not correlate with the high-sensitivity CRP value (P=0.103, Table 1).

DISCUSSION

In general, among patients with non-specific complaints of chest pain or the like, a patient determined as positive based on conventional indicators such as changes in electrocardiogram, high-sensitivity CRP value, and cardiac troponin T value is urgently taken to a specialized hospital because the patient is determined to have a high probability of development of a cardiovascular disease such as myocardial infarction. Further, even if there is no abnormality in wave shapes of the electrocardiogram, a patient with a previous history of typical thoracic symptom or with an arteriosclerotic risk factor may be suspected to have a disease such as angina and subjected to a thorough examination. However, the subject to be examined may be one who does not correspond to such patient but has a severe symptom such as a symptom immediately before complete occlusion of the coronary artery. That is, the related-art examination methods cannot distinguish patients with high accuracy. In addition, to achieve a positive troponin T value, it is necessary that the patient actually develop myocardial necrosis, i.e., myocardial infarction and that the positive value can be obtained after a lapse of several hours after the development. Therefore, in actuality, the examination method using troponin T gives a false negative result in many cases.

As shown in FIG. 14, even when the patients were classified into two groups of patients with high-sensitivity CRP values of 1 mg/L or more and patients with high-sensitivity CRP values of less than 1 mg/L, the plasma CyPA level was highly correlated with the presence or absence and severity of coronary artery disease in both the groups. Therefore, the results strongly suggest that the plasma CyPA level can be used to predict a cardiovascular disease, such as the presence or absence of significant coronary stenosis or probability of myocardial infarction, with high accuracy as compared to the related-art methods.

When the plasma CyPA level is used as a biomarker capable of screening a cardiovascular disease, such as a case which may develop systemic arteriosclerosis or myocardial infarction, it is expected to increase the number of lives saved more than ever before. In addition, the plasma CyPA level is expected to be useful for evaluation of a therapeutic effect.

The invention claimed is:

1. An examination kit for a cardiovascular disease, said kit comprising (i) means for measuring a concentration of cyclophilin A protein in a human blood sample and (ii) instructions for an examination method for a cardiovascular disease, the examination method comprising the steps of:
   measuring a concentration of cyclophilin A protein in a human blood sample using said means for measuring a concentration of cyclophilin A protein in a human blood sample; and
   determining a probability of development of a cardiovascular disease based on the measured concentration of cyclophilin A protein when the measured concentration of cyclophilin A protein is 15 ng/mL or more, wherein the cardiovascular disease comprises at least one kind selected from the group consisting of coronary organic stenosis, aortic aneurysm, and pulmonary hypertension.

2. The kit according to claim 1, wherein the determination step of the examination method comprises determining that the probability of development of a cardiovascular disease is high when the measured concentration of cyclophilin A protein is 15 ng/mL or more.

* * * * *